United States Patent
Kobayashi et al.

(10) Patent No.: US 11,627,976 B2
(45) Date of Patent: Apr. 18, 2023

(54) FORCE TRANSMISSION MECHANISM AND INSTRUMENT

(71) Applicant: OLYMPUS CORPORATION, Tokyo (JP)

(72) Inventors: Masayuki Kobayashi, Tokyo (JP); Noriaki Yamanaka, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 541 days.

(21) Appl. No.: 16/896,434

(22) Filed: Jun. 9, 2020

(65) Prior Publication Data
US 2020/0298419 A1    Sep. 24, 2020

Related U.S. Application Data

(63) Continuation of application No. PCT/JP2017/044275, filed on Dec. 11, 2017.

(51) Int. Cl.
*A61B 17/29* (2006.01)
*A61B 34/30* (2016.01)
*B25J 15/00* (2006.01)

(52) U.S. Cl.
CPC .............. *A61B 17/29* (2013.01); *A61B 34/30* (2016.02); *A61B 2017/2903* (2013.01);
(Continued)

(58) Field of Classification Search
CPC ........ B25J 15/00; B25J 15/0019; B25J 15/02; A61B 17/068; A61B 17/28;
(Continued)

(56) References Cited

U.S. PATENT DOCUMENTS

2005/0273084 A1    12/2005  Hinman et al.
2006/0129146 A1*    6/2006  Dycus ................ A61B 18/1445
                                                   606/51
(Continued)

FOREIGN PATENT DOCUMENTS

EP        2113210 A2    11/2009
EP        2389886 A1    11/2011
(Continued)

OTHER PUBLICATIONS

International Search Report dated Jan. 23, 2018 issued in PCT/JP2017/044275.

*Primary Examiner* — Sarah W Aleman
(74) *Attorney, Agent, or Firm* — Scully, Scott, Murphy & Presser, P.C.

(57) ABSTRACT

A force transmission mechanism includes a force adjuster that receives a driving force and that is configured to change a force transmission efficiency, and also includes a driving member that is configured to connect an end effector and the force adjuster via a joint section and transmit the driving force. The force adjuster converts the driving force into a linear force via a rotational force, and increases the conversion efficiency from the driving force to the linear force such that an amount of increase in the force transmission efficiency increases with increasing displacement amount of the driving member when the driving member is displaced in accordance with flexing or curving of the joint section.

10 Claims, 9 Drawing Sheets

(52) U.S. Cl.
CPC ............... *A61B 2017/2927* (2013.01); *A61B 2017/2933* (2013.01); *A61B 2017/2937* (2013.01); *B25J 15/0019* (2013.01)

(58) Field of Classification Search
CPC ..... A61B 17/2841; A61B 17/29; A61B 17/32; A61B 17/320016; A61B 2017/00398; A61B 2017/2902; A61B 2017/2903; A61B 2017/2912; A61B 2017/2913; A61B 2017/2916; A61B 2017/2927; A61B 2017/2932; A61B 2017/2933; A61B 2017/2939; A61B 2017/2941; A61B 2017/320092; A61B 2017/3201; A61B 18/1442; A61B 18/1445; A61B 2018/0063; A61B 2090/064; A61B 34/30; A61B 34/70; A61B 34/72; A61G 17/1622; A61G 17/1624
See application file for complete search history.

(56) References Cited

U.S. PATENT DOCUMENTS

| | | |
|---|---|---|
| 2009/0270853 A1 | 10/2009 | Yachi et al. |
| 2010/0179540 A1* | 7/2010 | Marczyk ............ A61B 18/1445 606/41 |
| 2011/0295313 A1 | 12/2011 | Kerr |
| 2012/0209314 A1* | 8/2012 | Weir ...................... A61B 34/37 606/205 |
| 2017/0325905 A1 | 11/2017 | Jogasaki et al. |
| 2017/0340320 A1* | 11/2017 | Baril ................ A61B 17/00234 |
| 2018/0092656 A1* | 4/2018 | Tuijthof ................. A61B 17/29 |
| 2019/0021757 A1* | 1/2019 | Kobayashi ......... A61B 18/1445 |
| 2019/0021784 A1* | 1/2019 | Kobayashi ......... A61B 18/1445 |
| 2019/0059987 A1* | 2/2019 | Shelton, IV ....... A61B 18/1445 |
| 2020/0039093 A1 | 2/2020 | Yamanaka |

FOREIGN PATENT DOCUMENTS

| | | |
|---|---|---|
| EP | 3001970 A1 | 4/2016 |
| JP | H05-296884 A | 11/1993 |
| JP | H11-000307 A | 1/1999 |
| JP | 2004-129871 A | 4/2004 |
| JP | 2008-501478 A | 1/2008 |
| JP | 2009-261911 A | 11/2009 |
| JP | 2011-245303 A | 12/2011 |
| JP | 2012-066102 A | 4/2012 |
| JP | 2013-240612 A | 12/2013 |
| WO | WO 2005/120327 A2 | 12/2005 |
| WO | WO 2016/166898 A1 | 10/2016 |
| WO | WO 2018/193500 A1 | 10/2018 |

* cited by examiner

FIG. 13C ns and a slider is used in Patent Literature 2.

FORCE TRANSMISSION MECHANISM AND INSTRUMENT

CROSS-REFERENCE TO RELATED APPLICATIONS

This is a continuation of International Application PCT/JP2017/044275, with an international filing date of Dec. 11, 2017, which is hereby incorporated by reference herein in its entirety.

TECHNICAL FIELD

The present invention relates to a force transmission mechanism and an instrument.

BACKGROUND ART

A known instrument in the related art includes an end effector provided at the distal end and an operation section provided at the proximal end, and transmits a driving force applied to the operation section by an operator to the end effector so as to cause the end effector to open and close (e.g., see Patent Literatures 1 and 2). As a force transmission member that transmits the driving force from the operation section to the end effector, a cable is used in Patent Literature 1, and a slider is used in Patent Literature 2.

CITATION LIST

Patent Literature

{PTL 1}
Japanese Unexamined Patent Application, Publication No. 2013-240612
{PTL 2}
Japanese Unexamined Patent Application, Publication No. 2009-261911

SUMMARY OF INVENTION

A first aspect of the present disclosure is directed to a force transmission mechanism that is provided in an instrument and that transmits a driving force to an end effector from a force generator. The instrument includes the end effector, a joint section that is configured to be flexed or curved, and the force generator that generates the driving force. The end effector, the joint section, and the force generator are arranged in sequence along a longitudinal axis from a distal end. The force transmission mechanism includes a force adjuster and a driving member. The force adjuster is disposed between the joint section and the force generator, transmits the driving force applied from the force generator, and is configured to change a force transmission efficiency. The driving member is configured to connect the end effector and the force adjuster via the joint section and transmit the driving force applied from the force adjuster to the end effector. The force adjuster converts the driving force into a linear force along the longitudinal axis via a rotational force around a rotational axis extending along the longitudinal axis. The force adjuster increases the conversion efficiency from the driving force to the linear force such that an amount of increase in the force transmission efficiency increases with increasing displacement amount of the driving member when the driving member is displaced along the longitudinal axis in accordance with flexing or curving of the joint section.

Another aspect of the present invention provides an instrument including an end effector, a joint section that is configured to be flexed or curved, a force generator that generates a driving force, and the force transmission mechanism according to the above aspect that transmits the driving force from the force generator to the end effector. The end effector, the joint section, and the force generator are arranged in sequence along a longitudinal axis from a distal end.

DESCRIPTION OF EMBODIMENTS

A force transmission mechanism 1 and an instrument 2 according to an embodiment of the present invention will be described below with reference to the drawings.

Figure 1:
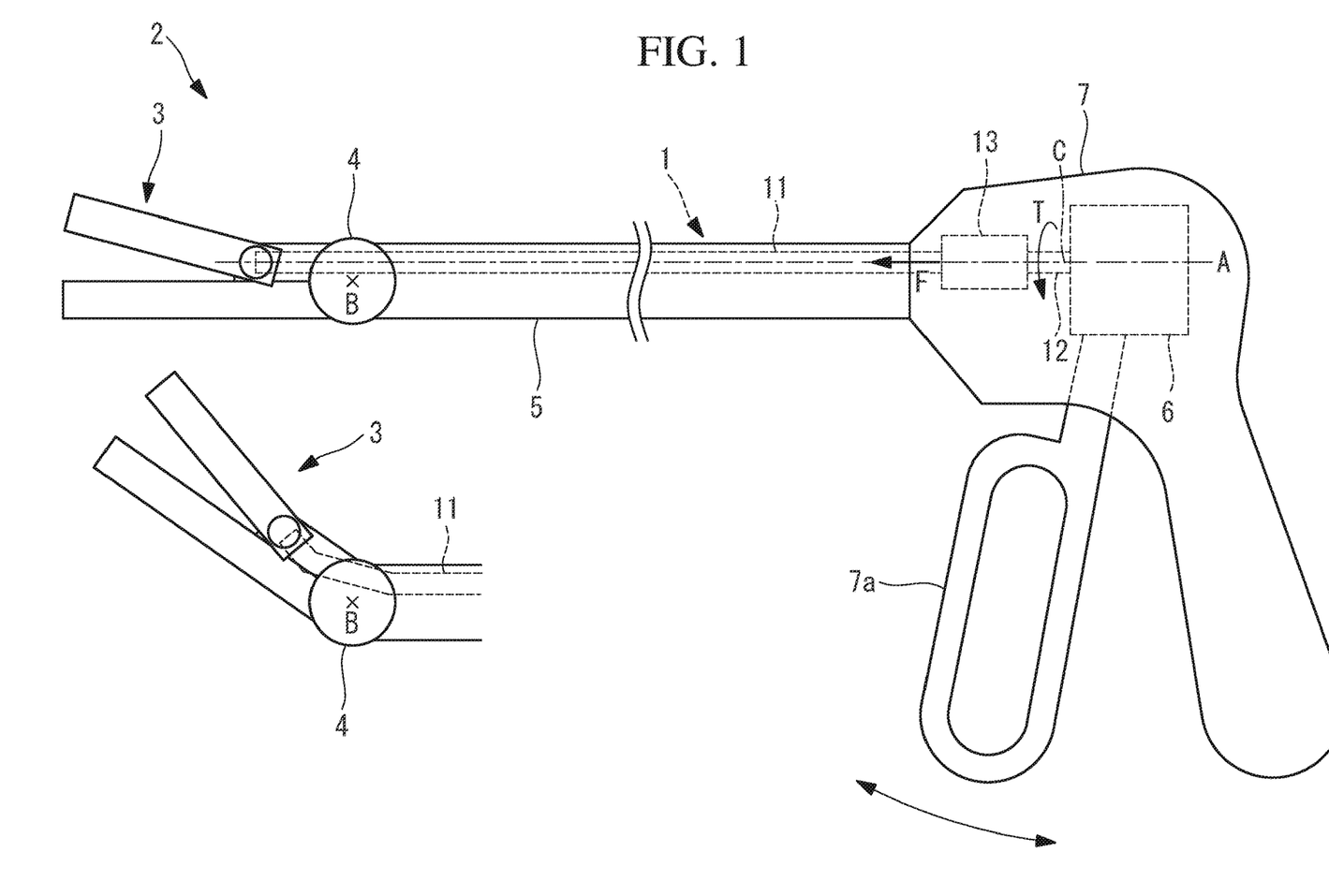
FIG. 1 illustrates the overall configuration of an instrument according to an embodiment of the present invention.

As shown in FIG. 1, the instrument 2 according to this embodiment includes an end effector 3, a joint section 4 flexed about a flexing axis B that is orthogonal to a longitudinal axis A, a narrow insertion section 5 insertable into the body and extending along the longitudinal axis A, and a force generator 6 that generates a driving force for driving the end effector 3. These components are arranged in sequence along the longitudinal axis A from the distal end.

The instrument 2 also includes a force transmission mechanism 1 that connects the end effector 3 and the force generator 6 by extending through the joint section 4 and the insertion section 5 and that transmits the driving force from the force generator 6 to the end effector 3.

The end effector 3 is gripping forceps having a pair of gripping segments that are openable and closable relative to each other, and can swing around the flexing axis B when the joint section 4 is flexed. The end effector 3 is configured to close in accordance with a pressing force transmitted from the force transmission mechanism 1 and acting toward the distal end, and is configured to open in accordance with a pulling force transmitted from the force transmission mechanism 1 and acting toward the proximal end. Therefore, the magnitude of gripping force generated by the end effector 3 is controlled by the pressing force from the force transmission mechanism 1.

The end effector 3 is not limited to gripping forceps, and may be an end effector of another type (e.g., a knife) that moves mechanically in accordance with a driving force. Alternatively, a joint section provided in the end effector 3 may be driven in accordance with the driving force from the force transmission mechanism 1.

The proximal end of the insertion section 5 is connected to an operation section 7 to be gripped by an operator, and the force generator 6 is provided inside the operation section 7. The operation section 7 is provided with a handle 7a that is manually operated by the operator for opening and closing the end effector 3, and another handle (not shown) that is manually operated by the operator for flexing the joint section 4.

The force generator 6 generates a rotational torque (rotational force) T as a driving force around a rotational axis C extending along the longitudinal axis A from an operating force applied to the handle 7a operated by the operator, and transmits the rotational torque T to a second driving member 12 (to be described later) of the force transmission mechanism 1. The force generator 6 generates rotational torque T in opposite directions when the handle 7a is operated in the closing direction of the end effector 3 and when the handle 7a is operated in the opening direction of the end effector 3. For example, the handle 7a used may be of a freely chosen type, such as a lever type or a rotary type. The force generator 6 is designed in accordance with the form of the handle 7a and is constituted by, for example, at least one gear that converts a swinging motion of the handle 7a into a rotating motion.

The force transmission mechanism 1 includes a first driving member 11, a second driving member 12, and a cylindrical cam mechanism 13. The first driving member 11 is disposed along the longitudinal axis A and is connected to the end effector 3. The second driving member 12 is connected to the force generator 6 and is rotatable around the rotational axis C in accordance with the rotational torque T applied from the force generator 6. The clyndrical cam mechanism 13 (i.e., force adjuster) links the first driving member 11 and the second driving member 12. Further, the clyndrical cam mechanism 13 (force adjuster) converts the rotational torque T applied to the second driving member 12 into a linear force F along the longitudinal axis A, transmits the linear force F to the first driving member 11, and is also capable of changing the force conversion efficiency from the rotational torque T to the linear force F.

The first driving member 11 is an elongated member extending along the longitudinal axis A from the end effector 3 to the insertion section 5 via the joint section 4. The distal end of the first driving member 11 is connected to the end effector 3. The first driving member 11 is configured to transmit a driving force with high efficiency in the longitudinal direction and is configured to be flexed or curved at the joint section 4. For example, the first driving member 11 is constituted by a plurality of links linked to each other in a swingable manner or by a wire having flexibility. The first driving member 11 advances toward the distal end so as to apply a pressing force (i.e., driving force) to the end effector 3 for closing the end effector 3. The first driving member 11 retracts toward the proximal end so as to apply a pulling force (i.e., driving force) to the end effector 3 for opening the end effector 3.

The second driving member 12 is a columnar or tubular member disposed along the longitudinal axis A. The proximal end of the second driving member 12 is connected to the force generator 6. The second driving member 12 is rotatable around the rotational axis C serving as the central axis thereof, and is supported within the operation section 7 in a non-movable manner in the longitudinal direction. The second driving member 12 is a rigid member so that the rotational torque T applied to the proximal end from the force generator 6 can be transmitted to the distal end without loss.

Figure 2:
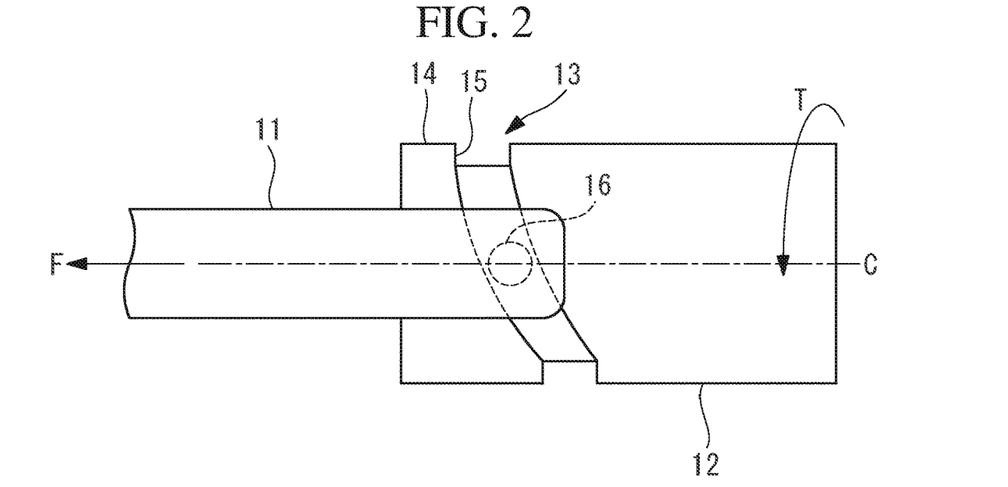
FIG. 2 schematically illustrates a cylindrical cam mechanism in a force transmission mechanism of the instrument in FIG. 1.

As shown in FIG. 2, the cylindrical cam mechanism 13 includes a cylindrical surface 14 and a cam pin 16. The cylindrical surface 14 has a cam groove 15 that is helical around the rotational axis C and rotates around the rotational axis C in an integrated manner with the second driving member 12. The cam pin 16 is fixed to the proximal end of the first driving member 11 and is inserted in the cam groove 15 in a movable manner in the extending direction of the cam groove 15.

The second driving member 12 rotates in accordance with the rotational torque T applied from the force generator 6. At this time, the cam pin 16 moves linearly along the longitudinal axis A by the helical cam groove 15 rotating around the rotational axis C. As a result, the linear motion acting along the longitudinal axis A is applied to the proximal end of the first driving member 11 via the cam pin 16. The cam groove 15 is configured to convert a rotating motion, occurring when the handle 7a is operated in the closing direction of the end effector 3, into a linear motion (i.e., pressing force) acting toward the distal end, and is configured to convert a rotating motion, occurring when the handle 7a is operated in the opening direction of the end effector 3, into a linear motion (i.e., pulling force) acting toward the proximal end.

Figure 3A:
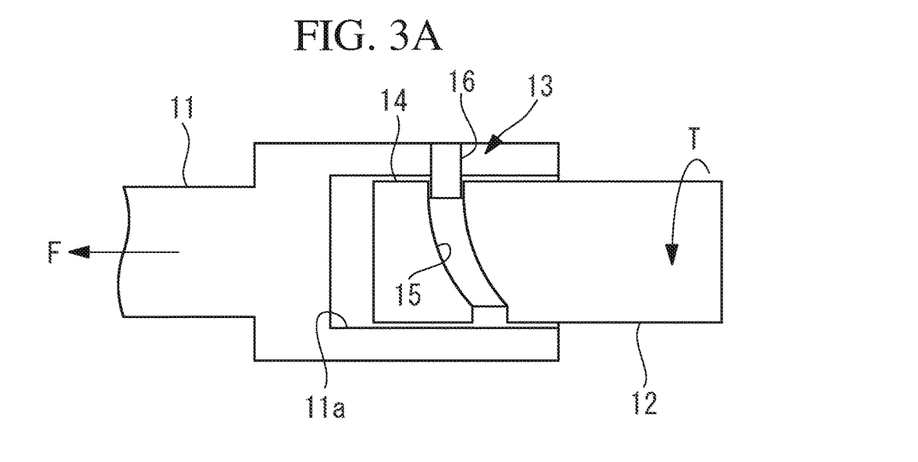
FIG. 3A illustrates a configuration example of the cylindrical cam mechanism in FIG. 2.

FIG. 3A illustrates a configuration example of the cylindrical cam mechanism 13. In the example in FIG. 3A, the cylindrical surface 14 is an outer surface at the distal end of the second driving member 12. The proximal end surface of the first driving member 11 has a hole 11a extending along the longitudinal axis A, and the distal end of the second driving member 12 is fitted in the hole 11a. The cam pin 16 is fixed to the proximal end of the first driving member 11 and protrudes radially inward from the inner surface of the hole 11a.

Figure 3B:
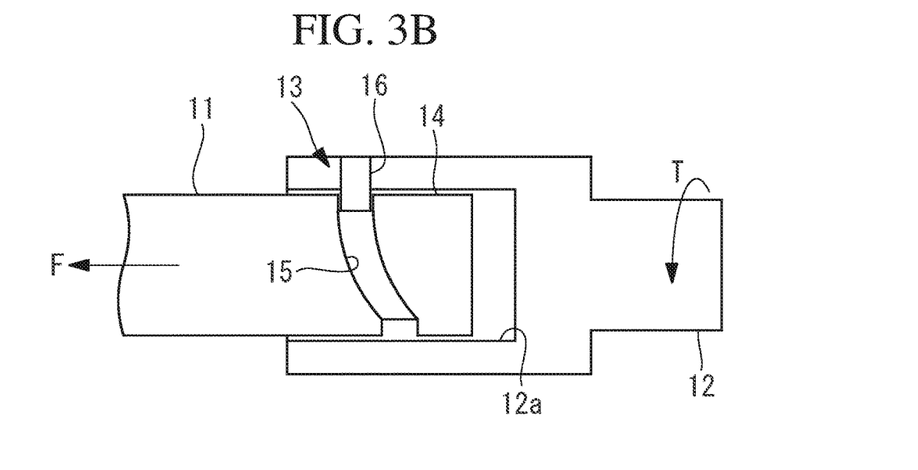
FIG. 3B illustrates another configuration example of the cylindrical cam mechanism in FIG. 2.

As shown in FIG. 3B, the cylindrical surface 14 and the cam groove 15 may be fixed to the first driving member 11, and the cam pin 16 may be rotated by the rotational torque T together with the second driving member 12.

In the example in FIG. 3B, the cylindrical surface 14 is an outer surface at the proximal end of the first driving member 11. The distal end surface of the second driving member 12 has a hole 12a extending along the longitudinal axis A, and the proximal end of the first driving member 11 is fitted in the hole 12a. The cam pin 16 is fixed to the distal end of the second driving member 12 and protrudes radially inward from the inner surface of the hole 12a.

In the example in FIGS. 3A and 3B, of the two driving members 11 and 12, the radially inner member is provided with the cylindrical surface 14 and the cam groove 15, and the radially outer member is provided with the cam pin 16. Alternatively, the radially inner member may be provided with the cam pin 16, and the radially outer member may be provided with the cylindrical surface 14 and the cam groove 15.

Next, the operation of the first driving member 11 and the cylindrical cam mechanism 13 when the joint section 4 is flexed around the flexing axis B, the force transmission efficiency of the first driving member 11, and the force conversion efficiency of the cylindrical cam mechanism 13 will be described.

Figure 4:
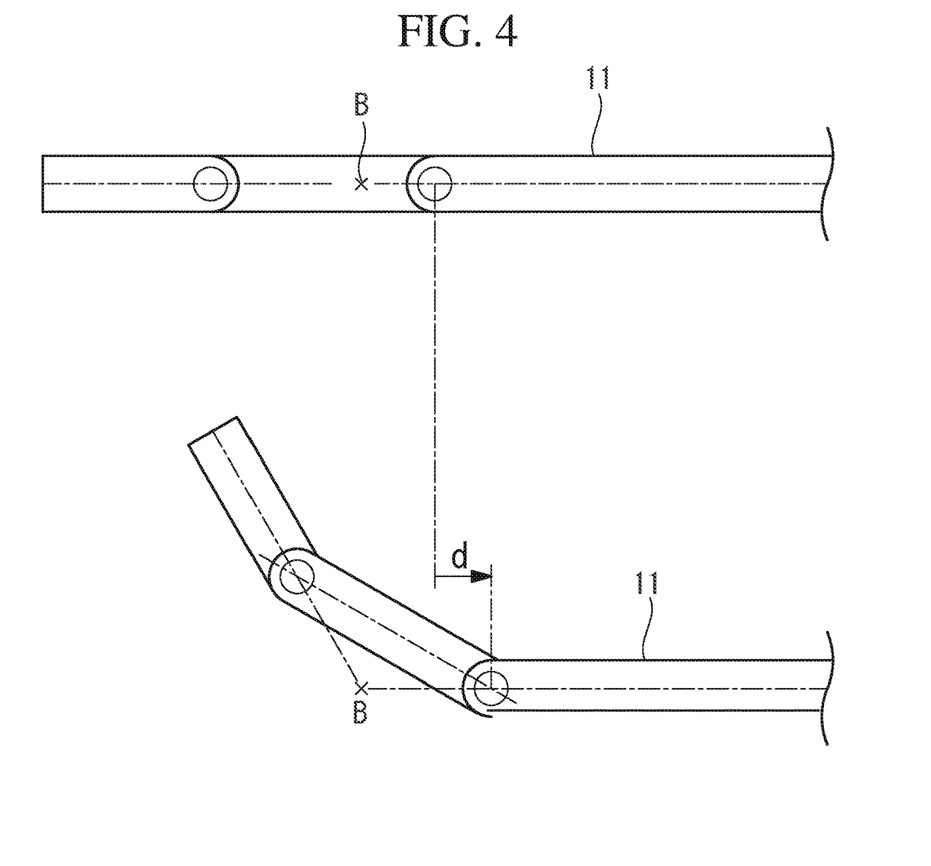
FIG. 4 is a configuration diagram of the force transmission mechanism of the instrument in FIG. 1, and illustrates the operation of the force transmission mechanism in a state where a joint section is not flexed (upper part) and a state where the joint section is flexed (lower part).

In FIG. 4, the upper part illustrates the joint section 4 in an unflexed state (i.e., a state where the end effector 3 and the insertion section 5 are arranged linearly on a straight line), and the lower part illustrates the joint section 4 in a flexed state. The position of the first driving member 11 when the end effector 3 is closed and the joint section 4 is not flexed will be defined as an initial position.

Figure 5:
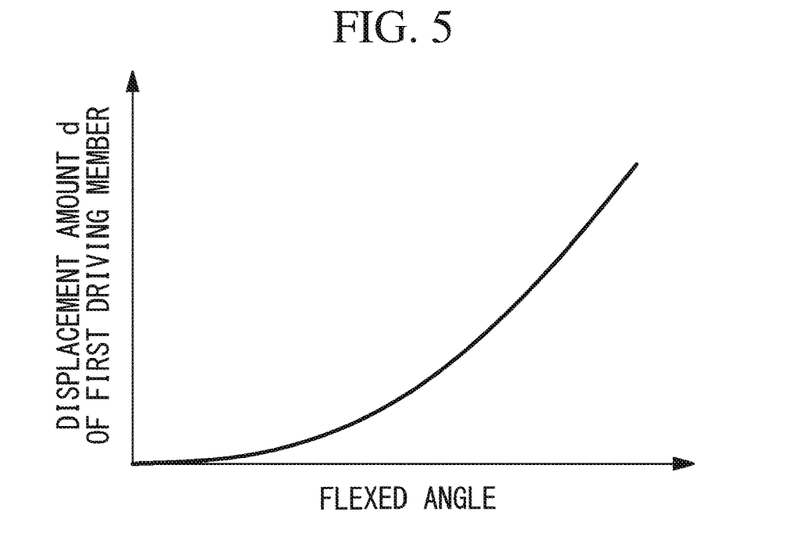
FIG. 5 is a graph illustrating the relationship between a flexed angle of the joint section and a displacement amount of a first driving member.

As shown in FIG. 4, when the joint section 4 flexes around the flexing axis B, the length of a path in which the first driving member 11 is disposed changes, and the first driving member 11 is displaced toward the proximal end from the initial position. In this case, the cam pin 16 fixed to the proximal end of the first driving member 11 is also displaced toward the proximal end while rotating the second driving member 12. As shown in FIG. 5, a displacement amount d of the first driving member 11 and the cam pin 16 from the initial position increases with increasing flexed angle of the joint section 4.

Figure 6:
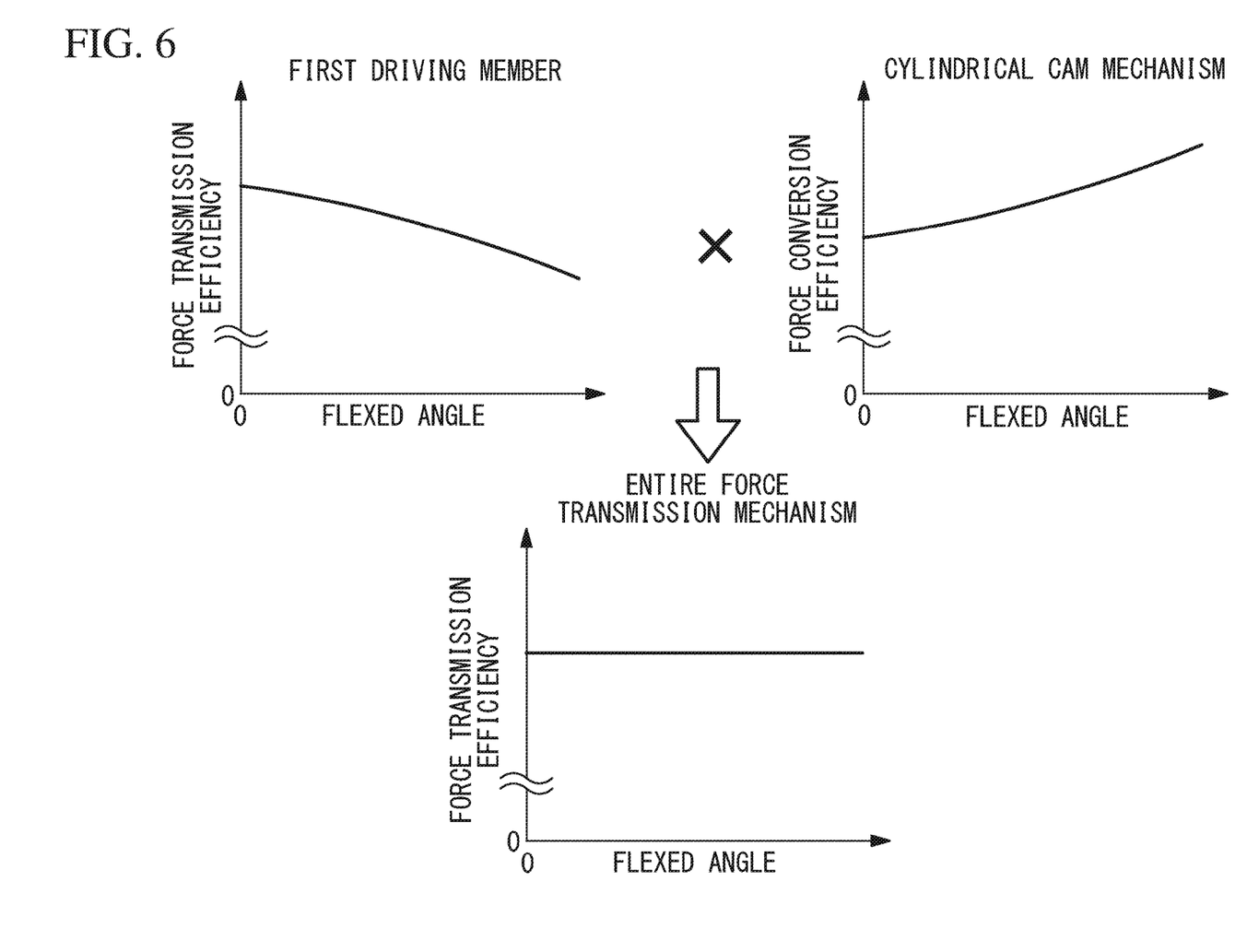
FIG. 6 is a graph illustrating the relationship among the flexed angle of the joint section, the force transmission efficiency of the first driving member, the force conversion efficiency of the cylindrical cam mechanism, and the force transmission efficiency of the entire force transmission mechanism.

FIG. 6 illustrates the force transmission efficiency of the first driving member 11, the force conversion efficiency of the cylindrical cam mechanism 13, and the force transmission efficiency of the entire force transmission mechanism 1, relative to a change in the flexed angle of the joint section 4. As shown in FIG. 6, when the joint section 4 is in a flexed state, the friction between the first driving member 11 flexed (or curved) together with the joint section 4 and a peripheral member increases as a result of an increase in contact between the first driving member 11 and the peripheral member. This causes the force transmission efficiency of the first driving member 11 to decrease. In a case where the first driving member 11 is constituted by a plurality of links, a decrease in the force transmission efficiency also occurs in accordance with the angle between the links. The amount of decrease in the force transmission efficiency of the first driving member 11 also increases with increasing flexed angle of the joint section 4.

The relationship between the magnitude of the rotational torque T applied to the proximal end of the second driving member 12 from the force generator 6 and the linear force F applied to the proximal end of the first driving member 11 from the cylindrical cam mechanism 13 is expressed with Expression (1) indicated below.

[Expression 1]

$$F = \frac{1 - \mu \tan\theta}{\tan\theta + \mu} \cdot \frac{1}{R} \cdot T \quad (1)$$

The coefficient $\alpha$ ($=\{(1-\mu \tan\theta)/(\tan\theta+\mu)\} \times 1/R$) of the rotational torque T in Expression (1) indicates the force conversion efficiency from the rotational torque T to the linear force F by the cylindrical cam mechanism 13 (i.e., the force transmission efficiency from the second driving member 12 to the first driving member 11). A force conversion efficiency $\alpha$ of the cylindrical cam mechanism 13 is dependent on a cam angle $\theta$, a cam radius R, and a cam friction coefficient $\mu$.

Figure 7:
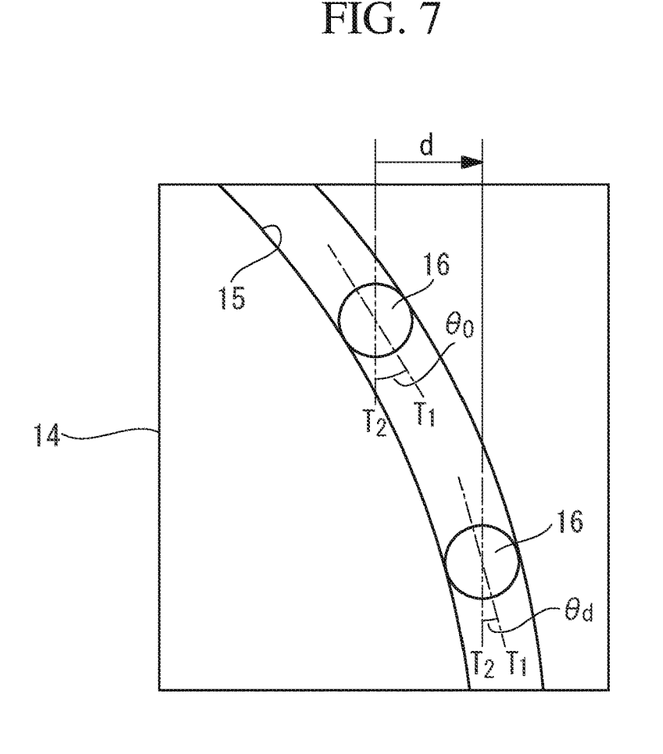
FIG. 7 is an example of a development view of a cylindrical surface of the cylindrical cam mechanism and illustrates a cam angle.

FIG. 7 is a cross-sectional development view of the cylindrical surface 14, taken along the rotational axis C. In FIG. 7, the vertical direction corresponds to the circumferential direction of the cylindrical surface 14, and the horizontal direction corresponds to the direction parallel to the rotational axis C of the cylindrical surface 14. As shown in FIG. 7, the cam groove 15 is curved in the development view, and the inclination of a tangent line of the cam groove 15 changes gradually from one end to the other end of the cam groove 15. The cam angle $\theta$ is the angle ($0°<\theta<90°$) formed by two tangent lines T1 and T2. The tangent line T1 is the tangent line of the cam groove 15 at the position of the cam pin 16. The tangent line T2 is the tangent line, at the position of the cam pin 16, of a circumference centered on the rotational axis C and extending through the cam pin 16, and is a vertical line extending through the position of the cam pin 16 in the development view.

Figure 8:
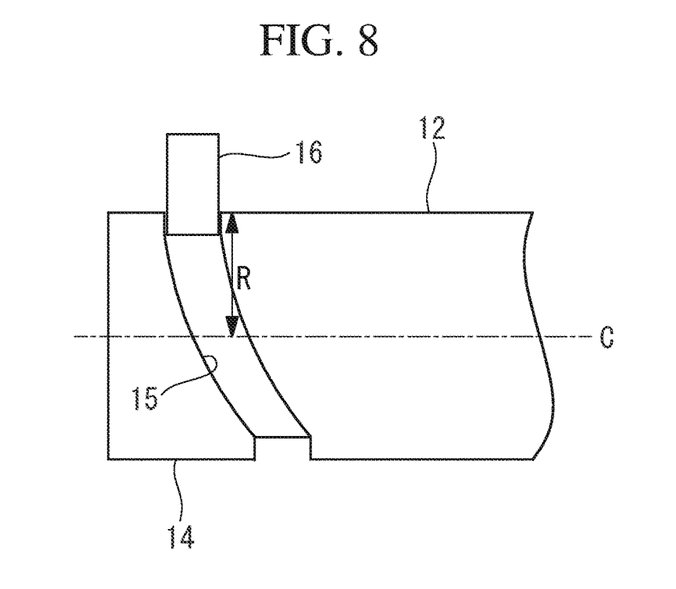
FIG. 8 is a side view of the cylindrical surface of the cylindrical cam mechanism and illustrates a cam radius.

FIG. 8 is a side view of the cylindrical surface 14 at the distal end of the second driving member 12. As shown in FIG. 8, the cam radius R is the radius of the cylindrical surface 14 at the position of the cam pin 16.

The cam friction coefficient $\mu$ is the friction coefficient between the inner surface of the cam groove 15 and the outer surface of the cam pin 16.

It is clear from Expression (1) that the force conversion efficiency $\alpha$ of the cylindrical cam mechanism 13 increases as the cam angle $\theta$, the cam radius R, and the cam friction coefficient $\mu$ decrease. Based on this relationship among the force conversion efficiency $\alpha$, the cam angle $\theta$, the cam radius R, and the cam friction coefficient $\eta$, the cylindrical cam mechanism 13 is configured to satisfy both of the following two points. First, the force conversion efficiency $\alpha$ increases in accordance with displacement of the cam pin 16 caused by flexing of the joint section 4. Second, the amount of increase in the force conversion efficiency $\alpha$ increases with increasing displacement amount d of the cam pin 16.

Specifically, when the first driving member 11 is disposed at the initial position, the cam pin 16 is disposed at a predetermined reference position within the cam groove 15. The curved shape of the cam groove 15 is designed to satisfy both of the following two points. First, a cam angle $\theta_d$ when the cam pin 16 is displaced from the reference position due to flexing of the joint section 4 is smaller than a cam angle $\theta_0$ when the cam pin 16 is disposed at the reference position. Second, the cam angle $\theta_d$ decreases with increasing displacement amount d of the cam pin 16 toward the proximal end.

Furthermore, the cylindrical surface 14 and the cam groove 15 are formed such that the cam radius R and the cam friction coefficient $\mu$ are constant, regardless of the position of the cam pin 16 within the cam groove 15.

Moreover, the amount of increase in the force conversion efficiency $\alpha$ of the cylindrical cam mechanism 13 is designed in view of the amount of decrease in the force transmission efficiency of the first driving member 11 such that the force conversion efficiency $\alpha$ of the cylindrical cam mechanism 13 is substantially equal to the reciprocal of the force transmission efficiency of the first driving member 11 at any flexed angle of the joint section 4. The force transmission efficiency of the entire force transmission mechanism 1 is expressed as the product of the force transmission efficiency of the first driving member 11 and the force conversion efficiency α of the cylindrical cam mechanism 13. Therefore, as shown in FIG. 6, the force transmission efficiency of the entire force transmission mechanism 1 is maintained constant regardless of the flexed angle of the joint section 4.

Next, the operation of the force transmission mechanism 1 and the instrument 2 having the above-described configuration will be described.

A medical treatment performed on an affected site by using the instrument 2 according to this embodiment involves inserting the insertion section 5 into the body so that the end effector 3 at the distal end is disposed near the affected site. Further, the operator operates the flexing handle of the operation section 7 to flex the joint section 4. This allows the operator to adjust the position of the end effector 3 relative to the affected site.

Then, the end effector 3 is opened by operating the handle 7a in the opening direction so that the affected site is disposed between the pair of gripping segments, and the end effector 3 is closed by operating the handle 7a in the closing direction, thereby gripping the affected site. At this time, a rotational torque T corresponding to the amount of operating force applied to the handle 7a in the closing direction is input to the second driving member 12 from the force generator 6. The rotational torque T is converted into a linear force F by the cylindrical cam mechanism 13, and the linear force F is transmitted to the end effector 3 from the first driving member 11. Accordingly, the end effector 3 grips the affected site with a gripping force having a magnitude equivalent to the amount of operating force applied to the handle 7a.

In this case, as shown in FIG. 6, the force transmission efficiency of the first driving member 11 decreases in the state where the joint section 4 is flexed, and the amount of decrease in the force transmission efficiency of the first driving member 11 increases with increasing flexed angle of the joint section 4. On the other hand, when the joint section 4 is flexed, the cam angle θ of the cylindrical cam mechanism 13 decreases due to displacement of the cam pin 16 from the reference position, thus causing the force conversion efficiency α of the cylindrical cam mechanism 13 to increase. As the flexed angle of the joint section 4 increases, the cam angle θ decreases, and the amount of increase in the force conversion efficiency α of the cylindrical cam mechanism 13 increases.

Accordingly, the decrease in the force transmission efficiency of the first driving member 11 occurring with the flexing of the joint section 4 is compensated for by the increase in the force conversion efficiency α of the cylindrical cam mechanism 13. As a result, the force transmission efficiency of the entire force transmission mechanism 1 is constant regardless of the flexed angle of the joint section 4. That is, the relationship between the amount of operating force applied to the handle 7a and the gripping force of the end effector 3 is maintained constant regardless of the flexed angle of the joint section 4. Accordingly, this is advantageous in that the operator can accurately control the gripping force in accordance with the amount of operating force applied to the handle 7a.

Furthermore, the cam angle θ, the cam radius R, and the cam friction coefficient μ of the cylindrical cam mechanism 13 can be designed independently of each other, and each have a high degree of design freedom. Accordingly, this is advantageous in terms of a simplified design for achieving a desired cam angle θ.

In this embodiment, the end effector 3 is closed by a pressing force and is opened by a pulling force. Alternatively, the end effector 3 may be closed by a pulling force and may be opened by a pushing force, and the magnitude of a gripping force generated by the end effector 3 may be controlled by a pulling force from the force transmission mechanism 1.

In this case, the force adjuster 13 is configured to convert a rotational torque T from the force generator 6 into a pulling force F when the handle 7a is operated in the closing direction. Referring to FIG. 2, for example, such a conversion process is realized by causing the cam groove 15 to tilt relative to the rotational axis C in the opposite direction from the direction shown in FIG. 2.

In this embodiment, the cam angle θ decreases in accordance with displacement of the first driving member 11 caused by flexing of the joint section 4. Alternatively, the cam radius R may decrease.

In a state where the cam pin 16 is displaced due to flexing of the joint section 4, the cam pin 16 is in contact with the inner surface of the cam groove 15. In this case, the conversion efficiency from the rotational torque T to the linear force F changes in accordance with the distance from the rotational axis C to the contact point between the cam pin 16 and the inner surface of the cam groove 15, that is, the cam radius R.

Figure 9:
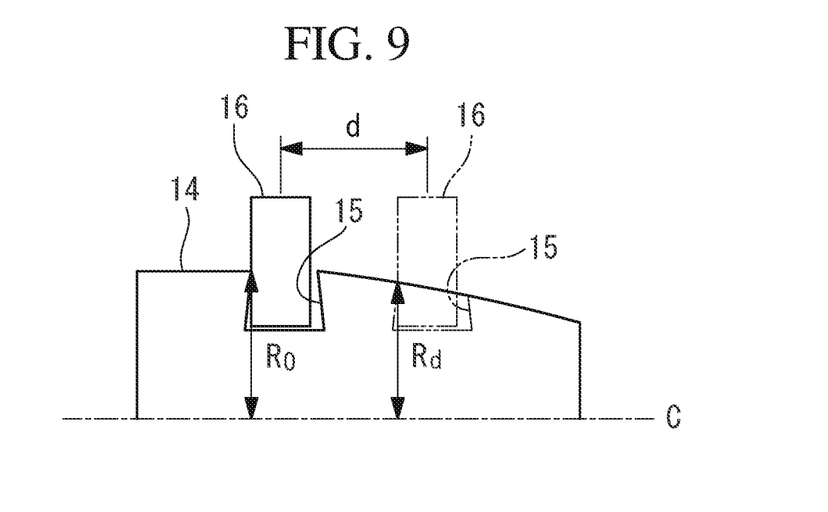
FIG. 9 is a side view of the cylindrical surface in a modification of the cylindrical cam mechanism.

The radius of curvature of the cylindrical surface 14 is designed such that the cam radius R gradually decreases in the direction in which the cam pin 16 moves when the joint section 4 is flexed. Accordingly, as shown in FIG. 9, it is possible to change the cam radius R while satisfying the following two points. First, a cam radius $R_d$ when the cam pin 16 is displaced from the reference position due to flexing of the joint section 4 is smaller than a cam radius $R_0$ when the cam pin 16 is disposed at the reference position. Second, the cam radius $R_d$ decreases with increasing displacement amount d of the cam pin 16 toward the proximal end.

Alternatively, the cam friction coefficient μ may decrease instead of the cam angle θ.

Figure 10:
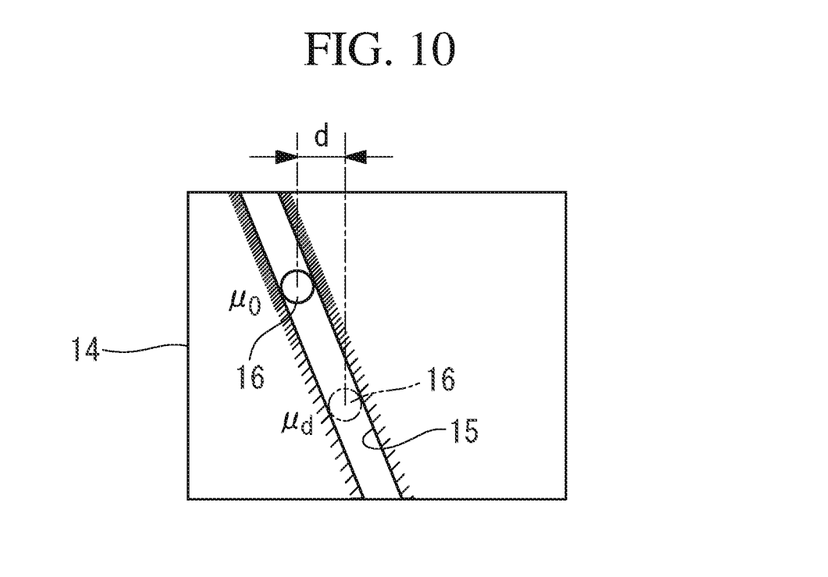
FIG. 10 is a development view of the cylindrical surface in another modification of the cylindrical cam mechanism.

Specifically, the cam friction coefficient μ is designed to gradually decrease in the direction in which the cam pin 16 moves when the joint section 4 is flexed. Accordingly, as shown in FIG. 10, it is possible to change the cam friction coefficient μ so as to satisfy following two points. First, a cam friction coefficient $μ_d$ when the cam pin 16 is displaced from the reference position due to flexing of the joint section 4 is smaller than a cam friction coefficient $μ_0$ when the cam pin 16 is disposed at the reference position. Second, the cam friction coefficient $μ_d$ decreases with increasing displacement amount d of the cam pin 16 toward the proximal end.

The cylindrical cam mechanism 13 may be configured such that two or more parameters among the three parameters, namely, the cam angle θ, the cam radius R, and the cam friction coefficient μ, change simultaneously when the joint section 4 is flexed.

In this case, not all of the two or more parameters have to decrease when the joint section 4 is flexed, so long as the two or more parameters change to satisfy Expression (2) indicated below. For example, one of the two parameters may decrease when the joint section 4 is flexed, whereas the other parameter may increase when the joint section 4 is flexed.

[Expression 2]

$$\frac{1-\mu_0\tan\theta_0}{\tan\theta_0+\mu_0}\cdot\frac{1}{R} < \frac{1-\mu_d\tan\theta_d}{\tan\theta_d+\mu_d}\cdot\frac{1}{R_d} \quad (2)$$

In this embodiment, the force generator 6 generates a rotational torque T as a driving force, and the rotational torque T is converted into a linear force F by a single cylindrical cam mechanism 13. Alternatively, the force generator 6 may generate a linear force as a driving force.

Figure 11:
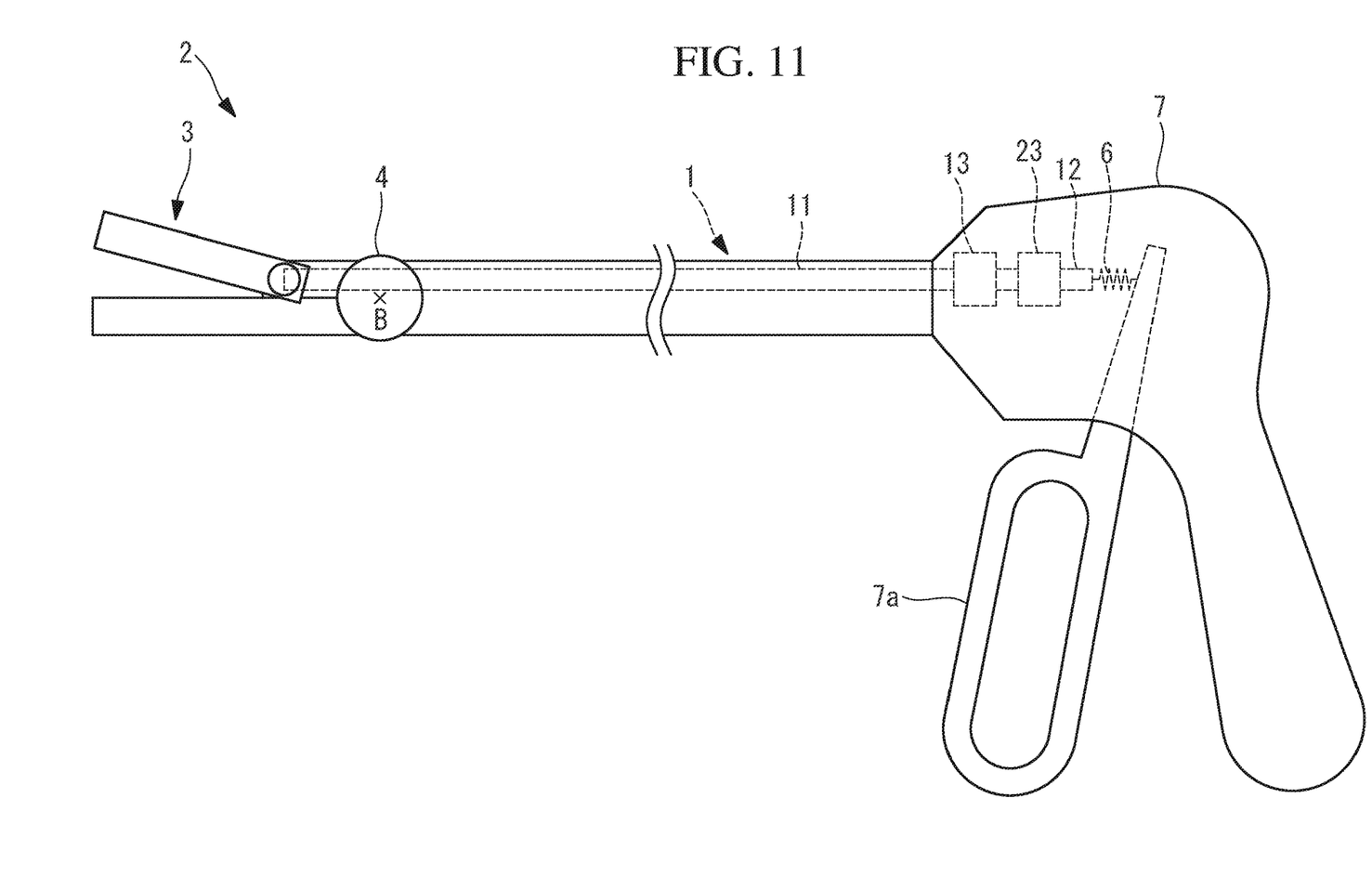
FIG. 11 is an overall configuration diagram of a modification of the instrument in FIG. 1.

FIG. 11 illustrates an example of a force generator 6 that generates a linear force. In this example, the force generator 6 includes a spring that expands and contracts in response to swinging of the handle 7a so as to generate a linear force $F_{in}$. In a case where the force generator 6 generates the linear force $F_{in}$, a force-direction conversion mechanism (i.e., force adjuster) that converts the linear force $F_{in}$ into a rotational torque T is further provided. The force-direction conversion mechanism is, for example, a gear or a cylindrical cam mechanism.

Figure 12:
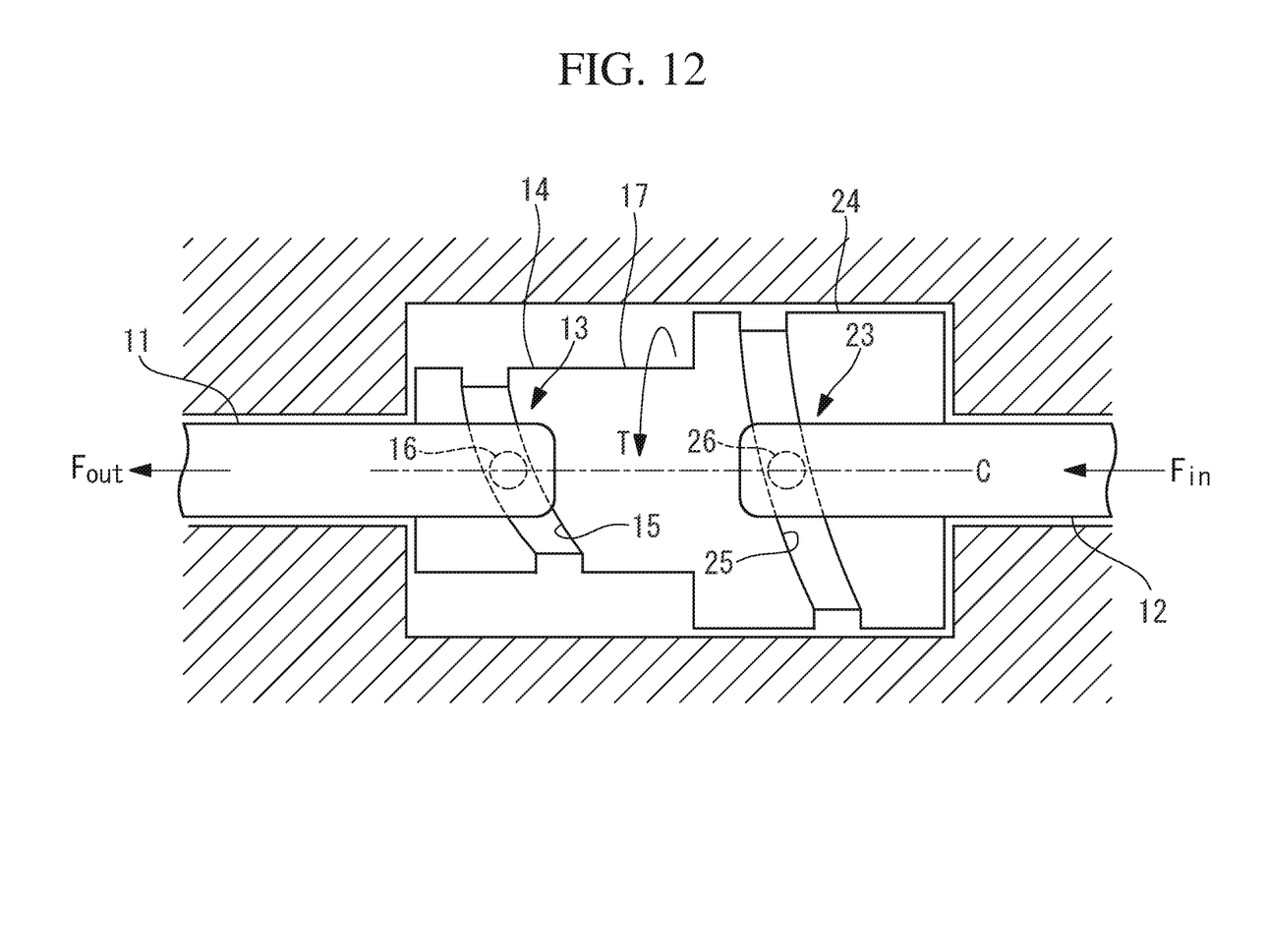
FIG. 12 schematically illustrates two cylindrical cam mechanisms in the force transmission mechanism of the instrument in FIG. 11.

FIG. 12 illustrates the configuration of another cylindrical cam mechanism (i.e., force adjuster, second cylindrical cam mechanism) 23, as an example of the force-direction conversion mechanism, different from the cylindrical cam mechanism (first cylindrical cam mechanism) 13.

A rotational member 17 that is rotatable around the rotational axis C is disposed between the first driving member 11 and the second driving member 12. The first cylindrical cam mechanism 13 links the first driving member 11 and the rotational member 17. The second cylindrical cam mechanism 23 links the rotational member 17 and the second driving member 12.

The first cylindrical cam mechanism 13 includes the cylindrical surface 14 serving as a cylindrical outer surface at the distal end of the rotational member 17 and having the cam groove 15, and also includes the cam pin 16 fixed to the first driving member 11.

The second cylindrical cam mechanism 23 includes a cylindrical surface 24 and a cam pin 26. The cylindrical surface 24 serves as a cylindrical outer surface at the proximal end of the rotational member 17 and has a cam groove 25 helical around the rotational axis C. The cam pin 26 is fixed to the second driving member 12 and is inserted in the cam groove 25 in a movable manner.

The linear force $F_{in}$ applied to the second driving member 12 from the force generator 6 is converted into a rotational torque T by the second cylindrical cam mechanism 23, and the rotational torque T is subsequently converted into a linear force $F_{out}$ by the first cylindrical cam mechanism 13.

In such a double cylindrical cam method, the relationship between the magnitude of the linear force $F_{in}$ applied to the second driving member 12 from the force generator 6 and the magnitude of the linear force $F_{out}$ applied to the proximal end of the first driving member 11 from the first cylindrical cam mechanism 13 is expressed with Expression (3) indicated below.

[Expression 3]

$$F_{out} = \frac{(\tan\theta_2-\mu_2)(1-\mu_1\tan\theta_1)}{(\tan\theta_1-\mu_1)(1-\mu_2\tan\theta_2)}\cdot\frac{R_2}{R_1}\cdot F_{in} \quad (3)$$

In Expression (3), $\theta_1$, $R_1$, and $\mu_1$ respectively indicate the cam angle $\theta$, the cam radius R, and the cam friction coefficient $\mu$ of the first cylindrical cam mechanism 13 described above.

$\theta_2$, $R_2$, and $\mu_2$ respectively indicate a cam angle, a cam radius, and a cam friction coefficient of the second cylindrical cam mechanism 23. The cam angle $\theta_2$ is the angle formed by a tangent line of the cam groove 25 at the position of the cam pin 26 and a tangent line, at the cam pin 26, of a circumference centered on the rotational axis C and extending through the cam pin 26. The cam radius $R_2$ is the radius of the cylindrical surface 24 at the position of the cam pin 26. The cam friction coefficient $\mu_2$ is the friction coefficient between the inner surface of the cam groove 25 and the outer surface of the cam pin 26.

The overall force conversion efficiency from the linear force Fin to the linear force $F_{out}$ by the two cylindrical cam mechanisms 13 and 23 is the coefficient of the linear force $F_{in}$ in Expression (3), and is dependent on the six parameters $\theta_1$, $\theta_2$, $R_1$, $R_2$, $\mu_1$, and $\mu_2$. The force conversion efficiency from the linear force $F_{in}$ to the rotational torque T by the second cylindrical cam mechanism 23 increases as the cam angle $\theta_2$, the cam radius $R_2$, and the cam friction coefficient $\mu_2$ increase.

At least one of the six parameters $\theta_1$, $\theta_2$, $R_1$, $R_2$, $\mu_1$, and $\mu^2$ is designed such that the overall force conversion efficiency of the cylindrical cam mechanisms 13 and 23 increases in accordance with displacement of the first driving member 11 caused by flexing of the joint section 4. In some embodiments, at least one of these six parameters is designed such that the overall force conversion efficiency of the cylindrical cam mechanism 13 and 23 is substantially equal to the reciprocal of the force transmission efficiency of the first driving member 11.

For example, by designing the cam angle $\theta_1$ to be a small value, the rotational stroke of the rotational member 17 increases, and the cam radius $R_2$ and the cam angle $\theta_2$ can be designed to increase when the joint section 4 is flexed.

Figure 13A:
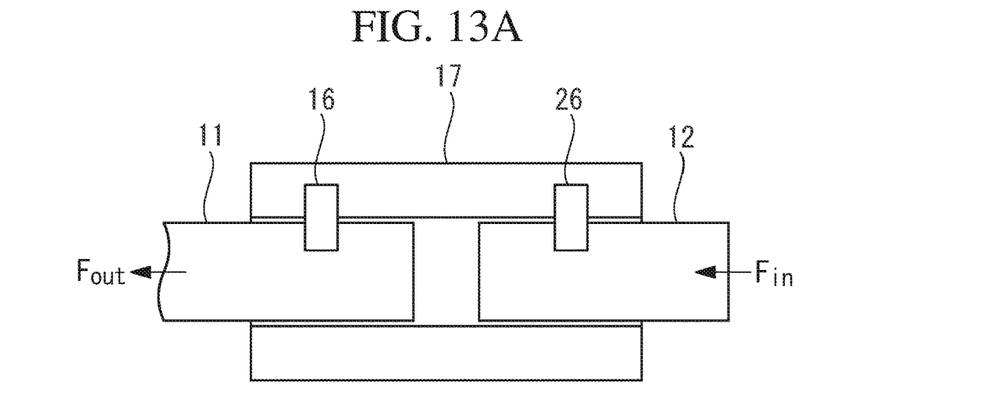
FIG. 13A illustrates a configuration example of the two cylindrical cam mechanisms in FIG. 12.
Figure 13B:
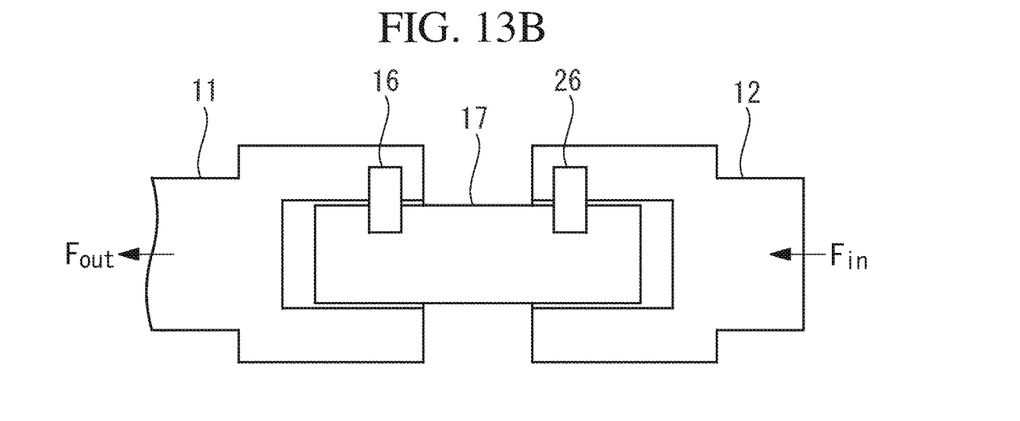
FIG. 13B illustrates another configuration example of the two cylindrical cam mechanisms in FIG. 12.
Figure 13C:
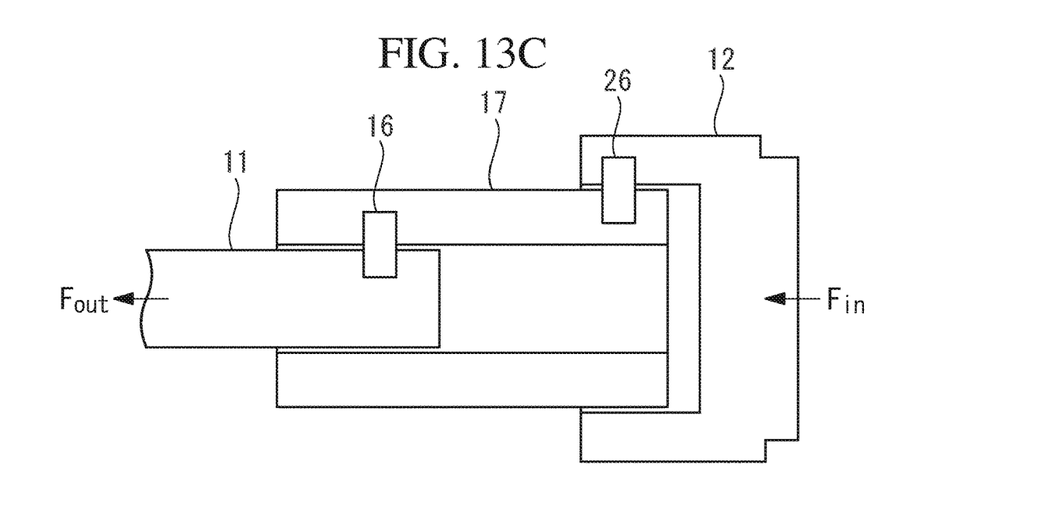
FIG. 13C illustrates another configuration example of the two cylindrical cam mechanisms in FIG. 12.

FIGS. 13A to 13C schematically illustrate the arrangement of the driving members 11 and 12 and the rotational member 17.

In the example in FIG. 13A, the rotational member 17, which is tubular, is disposed at the radially outer side of the first and second driving members 11 and 12. In the example in FIG. 13B, the rotational member 17, which is columnar, is disposed at the radially inner side of the first and second driving members 11 and 12. In the example in FIG. 13C, the rotational member 17, which is tubular, is disposed at the radially inner side of the second driving member 12, and the first driving member 11 is disposed at the radially inner side of the rotational member 17.

The cylindrical surfaces 14 and 24 and the cam grooves 15 and 25 are provided in one of the radially inner member and the radially outer member, and the cam pins 16 and 26 are provided in the other one of the radially inner member and the radially outer member. In some embodiments, the cylindrical surfaces 14 and 24 and the cam grooves 15 and 25 are provided in the inner member, and the cam pins 16 and 26 are provided in the outer member.

In this embodiment, the joint section 4 provided has a single flexing axis B. However, the specific configuration of the joint section 4 is not limited to this. Another type of joint section that may be used may be flexed or curved in a direction intersecting the longitudinal axis of the insertion section 5.

For example, the joint section may be a curving section that has a plurality of flexing axes arranged along the longitudinal axis A and parallel to each other and that is curvable with a relatively large radius of curvature, or may be a curving section that has flexibility and is curvable.

Furthermore, the joint section may be the insertion section 5 having flexibility and may be configured such that the force transmission mechanism 1 increases the force transmission efficiency in accordance with the curved angle of the insertion section 5 inside the body. When the insertion section 5 deforms from a linear shape to a curved shape, the path length of the first driving member 11 serving as a wire extending through the insertion section 5 changes, thus causing the first driving member 11 to be displaced in the longitudinal direction. Consequently, for example, the force transmission mechanism 1 is provided at the proximal end of the insertion section 5 that is to be disposed outside the body. Thus, the decrease in the force transmission efficiency of the first driving member 11 caused when the insertion section 5 is curved due to displacement of the first driving member 11 can be compensated for by an increase in the force transmission efficiency of the force transmission mechanism 1.

As an alternative to this embodiment provided with the operation section 7 that generates a driving force by being manually operated by the operator, a driver that generates a driving force by using an electric motor may be used as a force generator. For example, an operation input device (not shown) separate from the instrument 2 may be provided. When an operation signal for moving the end effector 3 is input to the operation input device by the operator, the input operation signal may be transmitted to the driver from the operation input device, and the electric motor may generate a driving force corresponding to the operation signal.

The above-described embodiment leads to the following aspects.

A first aspect of the present disclosure is directed to a force transmission mechanism that is provided in an instrument and that transmits a driving force to an end effector from a force generator. The instrument includes the end effector, a joint section that is configured to be flexed or curved, and the force generator that generates the driving force. The end effector, the joint section, and the force generator are arranged in sequence along a longitudinal axis from a distal end. The force transmission mechanism includes a force adjuster and a driving member. The force adjuster is disposed between the joint section and the force generator, transmits the driving force applied from the force generator, and is configured to change a force transmission efficiency. The driving member is configured to connect the end effector and the force adjuster via the joint section and transmit the driving force applied from the force adjuster to the end effector. The force adjuster converts the driving force into a linear force along the longitudinal axis via a rotational force around a rotational axis extending along the longitudinal axis. The force adjuster increases the conversion efficiency from the driving force to the linear force such that an amount of increase in the force transmission efficiency increases with increasing displacement amount of the driving member when the driving member is displaced along the longitudinal axis in accordance with flexing or curving of the joint section.

According to the first aspect of the disclosure, the driving force is input from the force generator to the force adjuster. The driving force is converted into a linear force along the longitudinal axis via the rotational force by the force adjuster. In addition, the linear force is transmitted to the end effector from the force adjuster via the driving member. This allows the end effector to perform mechanical movements.

In this case, when the joint section is flexed or curved, the driving member disposed across the joint section is also flexed or curved, so that the driving member is displaced along the longitudinal axis of the instrument, and the force transmission efficiency decreases. Then, in response to the displacement of the driving member, the conversion efficiency from the driving force to the linear force by the force adjuster increases such that the force transmission efficiency of the force adjuster increases with increasing displacement amount of the driving member.

The displacement amount of the driving member and the amount of decrease in the force transmission efficiency both increase with increasing flexed or curved angle of the joint section. Therefore, by increasing the amount of increase in the force transmission efficiency of the force adjuster in accordance with the displacement amount of the driving member, a decrease in the force transmission efficiency of the driving member can be favorably compensated for by an increase in the force transmission efficiency of the force adjuster. Consequently, the driving force can be transmitted to the end effector with constant efficiency regardless of flexing or curving of the joint section.

In the above aspect, the force adjuster may change the force transmission efficiency such that the force transmission efficiency of the force adjuster is substantially equal to a reciprocal of a force transmission efficiency of the driving member.

The force transmission efficiency of the entire force transmission mechanism is expressed as the product of the force transmission efficiency of the force adjuster and the force transmission efficiency of the driving member. Therefore, the force transmission efficiency of the force adjuster increases so as to become substantially equal to the reciprocal of the force transmission efficiency of the driving member, which has decreased due to flexing or curving of the joint section. As a result, the force transmission efficiency of the entire force transmission mechanism can be kept more accurately constant, regardless of flexing or curving of the joint section.

In the above aspect, the force adjuster may include a cylindrical cam mechanism that converts the rotational force into the linear force. The cylindrical cam mechanism has a cylindrical surface with a cam groove that is helical around the rotational axis and also has a cam pin that moves within the cam groove. One of the cylindrical surface and the cam pin is rotated around the rotational axis by the rotational force, and the other one of the cylindrical surface and the cam pin is fixed to the driving member.

Accordingly, the rotational force can be converted into the linear force with a simple configuration.

In the above aspect, the cylindrical cam mechanism may be configured such that a cam radius from the rotational axis to the cylindrical surface at a position of the cam pin decreases as the displacement amount of the driving member according to flexing or curving of the joint section increases.

The force conversion efficiency from the rotational force to the linear force by the cylindrical cam mechanism increases with decreasing cam radius. Therefore, by forming the cylindrical surface of the cylindrical cam mechanism such that the cam radius decreases in accordance with displacement of the driving member, the conversion efficiency of the cylindrical cam can be increased. Moreover, this increases the degree of design freedom for the cam radius, and allows for a simplified design for achieving a desired cam radius.

In the above aspect, the cylindrical cam mechanism may be configured such that a cam angle formed by a tangent line of the cam groove at a position of the cam pin and a tangent line of a circumference centered on the rotational axis at the position of the cam pin decreases as the displacement amount of the driving member according to flexing or curving of the joint section increases.

The force conversion efficiency from the rotational force to the linear force by the cylindrical cam mechanism increases with decreasing cam angle. Therefore, by forming the cam groove of the cylindrical cam mechanism such that the cam angle decreases in accordance with displacement of the driving member, the conversion efficiency of the cylindrical cam can be increased. Moreover, this increases the degree of design freedom for the cam groove, and allows for a simplified design for achieving a desired cam angle.

In the above aspect, the cylindrical cam mechanism may be configured such that a cam friction coefficient between an inner surface of the cam groove and an outer surface of the cam pin decreases as the displacement amount of the driving member according to flexing or curving of the joint section increases.

The force conversion efficiency from the rotational force to the linear force by the cylindrical cam mechanism increases with decreasing cam friction coefficient. Therefore, by forming the inner surface of the cam groove of the cylindrical cam mechanism such that the cam friction coefficient decreases in accordance with displacement of the driving member, the conversion efficiency of the cylindrical cam can be increased. Moreover, this increases the degree of design freedom for the cam friction coefficient, and allows for a simplified design for achieving a desired cam friction coefficient.

In the above aspect, the force adjuster may include a force-direction conversion mechanism that is disposed between the force generator and the cylindrical cam mechanism and that converts the driving force generated by the force generator and acting along the rotational axis into the rotational force.

Accordingly, the force-direction conversion mechanism can be suitably combined with the force generator that generates a linear force as a driving force along the longitudinal axis.

In the above aspect, the force-direction conversion mechanism may be a second cylindrical cam mechanism that converts the driving force into the rotational force.

Accordingly, the linear force can be converted into the rotational force with a simple configuration.

In the above aspect, the force adjuster may change at least one of cam radii, cam angles, and cam friction coefficients of the cylindrical cam mechanism and the second cylindrical cam mechanism such that the force transmission efficiency of the force adjuster is substantially equal to a reciprocal of a force transmission efficiency of the driving member.

Accordingly, by changing at least one of the cam radii, the cam angles, and the cam friction coefficients of the two cylindrical cam mechanisms, the force transmission efficiency of the force adjuster can be increased with a simple configuration.

Another aspect of the present invention provides an instrument including an end effector, a joint section that is configured to be flexed or curved, a force generator that generates a driving force, and the force transmission mechanism according to the above aspect that transmits the driving force from the force generator to the end effector. FThe end effector, the joint section, and the force generator are arranged in sequence along a longitudinal axis from a distal end.

The present invention is advantageous in that it can transmit a driving force to an end effector with constant efficiency regardless of flexing or curving of a joint section.

REFERENCE SIGNS LIST 1 force transmission mechanism
2 instrument
3 end effector
4 joint section
5 insertion section
6 force generator
7 operation section
7a handle
11 first driving member (driving member)
12 second driving member
13 cylindrical cam mechanism (force adjuster)
23 cylindrical cam mechanism (force adjuster, force-direction conversion mechanism)
14, 24 cylindrical surface
15, 25 cam groove
16, 26 cam pin
17 rotational member

The invention claimed is:

1. A force transmission mechanism that is provided in an instrument and that transmits a driving force to an end effector from a force generator, the instrument including the end effector, a joint section that is configured to be flexed or curved, and the force generator that generates the driving force, the end effector, the joint section, and the force generator being arranged in sequence along a longitudinal axis from a distal end, the force transmission mechanism comprising:
  a force adjuster that is disposed between the joint section and the force generator, the force adjuster transmitting the driving force applied from the force generator and that is configured to change a force transmission efficiency; and
  a driving member that is configured to connect the end effector and the force adjuster via the joint section and transmit the driving force applied from the force adjuster to the end effector,
  wherein the force adjuster converts the driving force into a linear force along the longitudinal axis via a rotational force around a rotational axis extending along the longitudinal axis, and
  wherein the force adjuster increases a conversion efficiency from the driving force to the linear force such that an amount of increase in the force transmission efficiency increases with increasing displacement amount of the driving member when the driving member is displaced along the longitudinal axis in accordance with flexing or curving of the joint section.

2. The force transmission mechanism according to claim 1,
  wherein the force adjuster changes the force transmission efficiency such that the force transmission efficiency of the force adjuster is substantially equal to a reciprocal of a force transmission efficiency of the driving member.

3. The force transmission mechanism according to claim 1,
  wherein the force adjuster comprises a cylindrical cam mechanism that converts the rotational force into the linear force, the cylindrical cam mechanism having a cylindrical surface with a cam groove that is helical around the rotational axis and also having a cam pin that moves within the cam groove, wherein one of the cylindrical surface and the cam pin is rotated around the rotational axis by the rotational force, and the other one of the cylindrical surface and the cam pin is fixed to the driving member.

4. The force transmission mechanism according to claim 3,
wherein the cylindrical cam mechanism is configured such that a cam radius from the rotational axis to the cylindrical surface at a position of the cam pin decreases as the displacement amount of the driving member according to flexing or curving of the joint section increases.

5. The force transmission mechanism according to claim 3,
wherein the cylindrical cam mechanism is configured such that a cam angle formed by a tangent line of the cam groove at a position of the cam pin and a tangent line of a circumference centered on the rotational axis at the position of the cam pin decreases as the displacement amount of the driving member according to flexing or curving of the joint section increases.

6. The force transmission mechanism according to claim 3,
wherein the cylindrical cam mechanism is configured such that a cam friction coefficient between an inner surface of the cam groove and an outer surface of the cam pin decreases as the displacement amount of the driving member according to flexing or curving of the joint section increases.

7. The force transmission mechanism according to claim 3,
wherein the force adjuster comprises a force-direction conversion mechanism that is disposed between the force generator and the cylindrical cam mechanism and that converts the driving force generated by the force generator and acting along the rotational axis into the rotational force.

8. The force transmission mechanism according to claim 7,
wherein the force-direction conversion mechanism comprises a second cylindrical cam mechanism that converts the driving force into the rotational force.

9. The force transmission mechanism according to claim 8,
wherein the force adjuster changes at least one of cam radii, cam angles, and cam friction coefficients of the cylindrical cam mechanism and the second cylindrical cam mechanism such that the force transmission efficiency of the force adjuster is substantially equal to a reciprocal of a force transmission efficiency of the driving member.

10. An instrument comprising:
an end effector, a joint section that is configured to be flexed or curved, and a force generator that generates a driving force, the end effector, the joint section, and the force generator being arranged in sequence along a longitudinal axis from a distal end; and
the force transmission mechanism according to claim 1 that transmits the driving force from the force generator to the end effector.

* * * * *